US012602781B2

(12) United States Patent (10) Patent No.: US 12,602,781 B2

Meyer (45) Date of Patent: Apr. 14, 2026

(54) AI-BASED CELL CLASSIFICATION METHOD AND SYSTEM

(71) Applicant: VisionGate, Inc., Woodinville, WA (US)

(72) Inventor: Michael G. Meyer, Phoenix, AZ (US)

(73) Assignee: VisionGate, Inc., Woodinville, WA (US)

( * ) Notice: Subject to any disclaimer, the term of this patent is extended or adjusted under 35 U.S.C. 154(b) by 440 days.

(21) Appl. No.: 18/361,752

(22) Filed: Jul. 28, 2023

(65) Prior Publication Data

US 2024/0212137 A1 Jun. 27, 2024

Related U.S. Application Data

(60) Provisional application No. 63/394,550, filed on Aug. 2, 2022.

(51) Int. Cl.
*G06T 7/00* (2017.01)
*G06T 17/00* (2006.01)
*G16H 50/20* (2018.01)

(52) U.S. Cl.
CPC ........... *G06T 7/0012* (2013.01); *G06T 17/00* (2013.01); *G16H 50/20* (2018.01); *G06T 2207/10101* (2013.01); *G06T 2207/20081* (2013.01); *G06T 2207/30024* (2013.01); *G06T 2207/30096* (2013.01)

(58) Field of Classification Search
CPC ................... G06T 7/0012; G06T 17/00; G06T 2207/10101; G06T 2207/20081; G06T 2207/30024; G06T 2207/30096; G16H 50/20
See application file for complete search history.

(56) References Cited

U.S. PATENT DOCUMENTS

| | | |
|---|---|---|
| 6,519,355 B2 | 2/2003 | Nelson |
| 6,522,775 B2 | 2/2003 | Nelson |
| 6,591,003 B2 | 7/2003 | Chu et al. |

(Continued)

FOREIGN PATENT DOCUMENTS

| | | |
|---|---|---|
| WO | 2005091203 A2 | 9/2005 |
| WO | 2017/053592 A1 | 3/2017 |
| WO | 2022101902 A1 | 5/2022 |

OTHER PUBLICATIONS

Meyer et al., "The Cell-CT 3D Cell Imaging Technology Platform Enables the Detection of Lung Cancer Using the Non-Invasive LuCED Sputum Test," *Cancer Cytopathol* 123(9):512-523, Sep. 2015. (29 pages).

(Continued)

*Primary Examiner* — Ming Shui

(74) *Attorney, Agent, or Firm* — Seed Intellectual Property Law Group LLP

(57) ABSTRACT

The present disclosure provides a system and method for AI-based cell classification of cells from a patient sample to determine if cells indicative of lung cancer are present. In the system and method, 2D imaging is used to eliminate cells not likely to be indicative of lung cancer from subsequent 3D imaging, while 3D imaging is conducted for cells likely to be indicative of lung cancer. The present disclosure further provides a method of training 2D cell classifiers for use in the system and method for AI-based cell classification.

21 Claims, 6 Drawing Sheets

(56) References Cited

U.S. PATENT DOCUMENTS

| | | | |
|---|---|---|---|
| 6,636,623 | B2 | 10/2003 | Nelson et al. |
| 6,697,508 | B2 | 2/2004 | Nelson |
| 7,197,355 | B2 | 3/2007 | Nelson |
| 7,494,809 | B2 | 2/2009 | Nelson et al. |
| 7,569,789 | B2 | 8/2009 | Hayenga et al. |
| 7,738,945 | B2 | 6/2010 | Fauver et al. |
| 7,787,112 | B2 | 8/2010 | Rahn et al. |
| 7,811,825 | B2 | 10/2010 | Fauver et al. |
| 7,835,561 | B2 | 11/2010 | Meyer et al. |
| 7,867,778 | B2 | 1/2011 | Hayenga et al. |
| 7,907,765 | B2 | 3/2011 | Fauver et al. |
| 7,933,010 | B2 | 4/2011 | Rahn et al. |
| 8,090,183 | B2 | 1/2012 | Meyer et al. |
| 8,155,420 | B2 | 4/2012 | Meyer et al. |
| 8,947,510 | B2 | 2/2015 | Meyer et al. |
| 9,594,072 | B2 | 3/2017 | Meyer et al. |
| 10,753,857 | B2 | 8/2020 | Steinhauer |
| 11,069,054 | B2 | 7/2021 | Nelson et al. |
| 2003/0031352 | A1 | 2/2003 | Nelson et al. |
| 2004/0076319 | A1 | 4/2004 | Fauver et al. |
| 2010/0088264 | A1 | 4/2010 | Teverovskiy et al. |
| 2010/0135566 | A1 | 6/2010 | Joanidopoulos et al. |
| 2017/0003267 | A1 | 1/2017 | Meyer et al. |
| 2017/0140533 | A1 | 5/2017 | Nelson et al. |
| 2018/0286038 | A1 | 10/2018 | Jalali et al. |
| 2020/0018704 | A1 | 1/2020 | Sussman et al. |
| 2020/0167914 | A1 | 5/2020 | Stamatoyannopoulos et al. |
| 2021/0049425 | A1* | 2/2021 | Meyer ............... G06V 10/7747 |
| 2021/0200987 | A1* | 7/2021 | Sussman ............... G06N 20/00 |
| 2021/0350113 | A1 | 11/2021 | Sjögren et al. |

OTHER PUBLICATIONS

Schapire et al., *Boosting: Foundations and Algorithms*, The MIT Press, Cambridge Massachusetts, London, England, 2012, 548 pages.

Lee et al., "Building predictive in vitro pulmonary toxicity assays using high-throughput imaging and artificial intelligence," *Archives of Toxicology* 92:2055-2075, 2018.

Meyer et al., "Automated cell analysis in 2D and 3D: A comparative study," Pattern Recognition 42: 141-146, 2009.

Meyer et al., "The Cell-CT 3-Dimensional Cell Imaging Technology Platform Enables the Detection of Lung Cancer Using the Noninvasive LuCED Sputum Test," Cancer (Cancer Cytopathol) 123: 512-523, 2015.

* cited by examiner

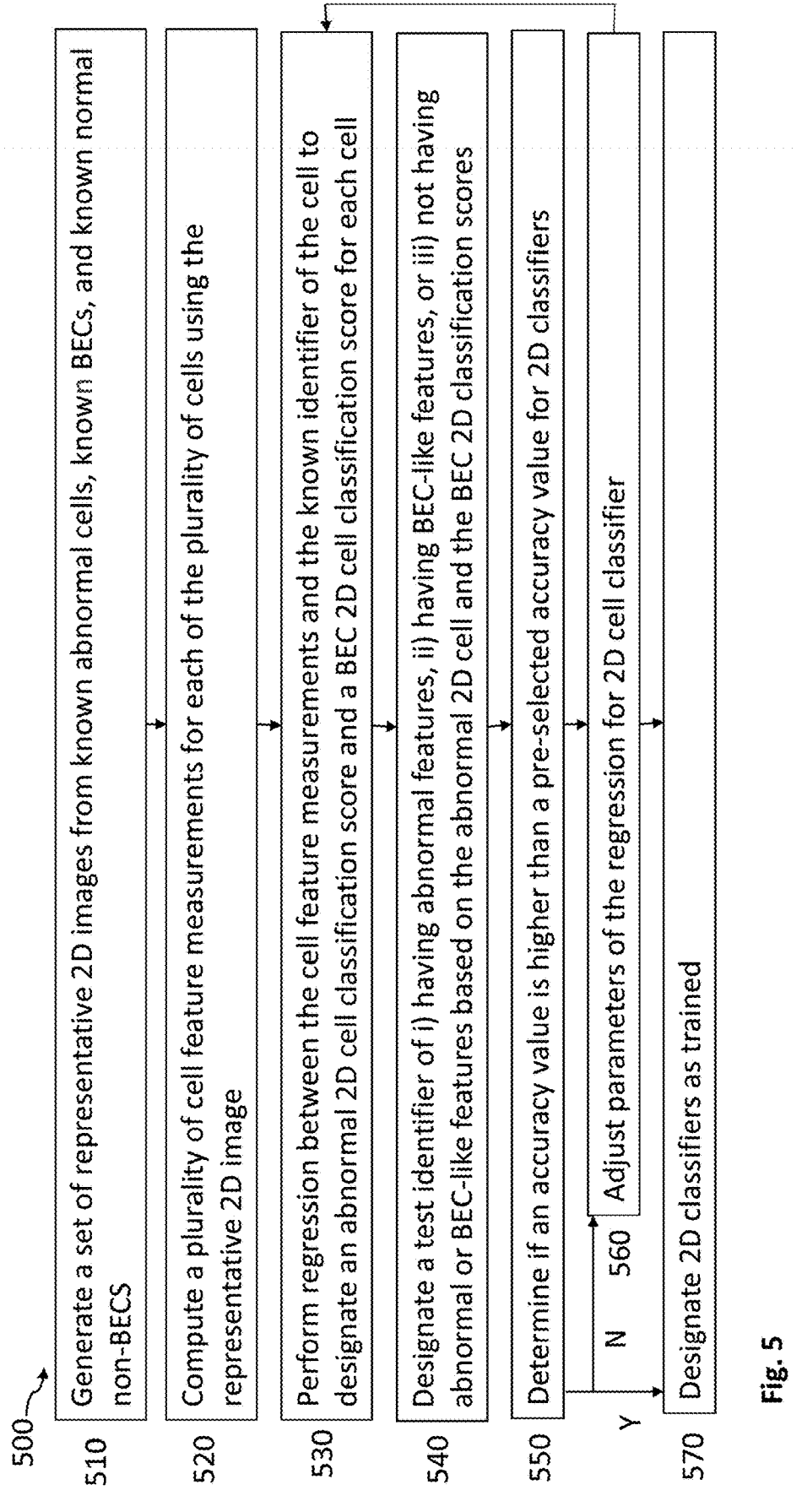

500

510 Generate a set of representative 2D images from known abnormal cells, known BECs, and known normal non-BECS 520 Compute a plurality of cell feature measurements for each of the plurality of cells using the representative 2D image 530 Perform regression between the cell feature measurements and the known identifier of the cell to designate an abnormal 2D cell classification score and a BEC 2D cell classification score for each cell 540 Designate a test identifier of i) having abnormal features, ii) having BEC-like features, or iii) not having abnormal or BEC-like features based on the abnormal 2D cell and the BEC 2D classification scores 550 Determine if an accuracy value is higher than a pre-selected accuracy value for 2D classifiers N 560 Adjust parameters of the regression for 2D cell classifier

Y

570 Designate 2D classifiers as trained

Fig. 5

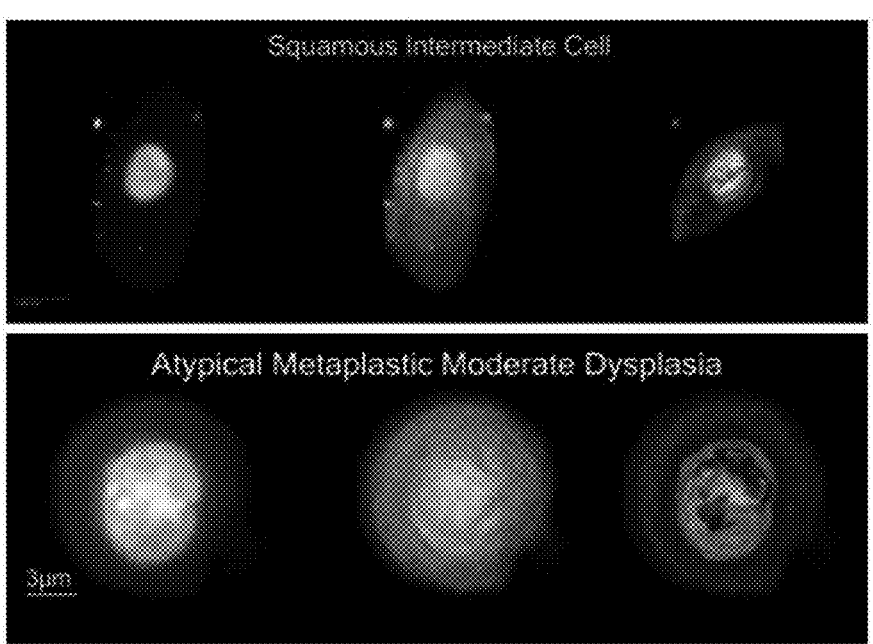
Fig. 6
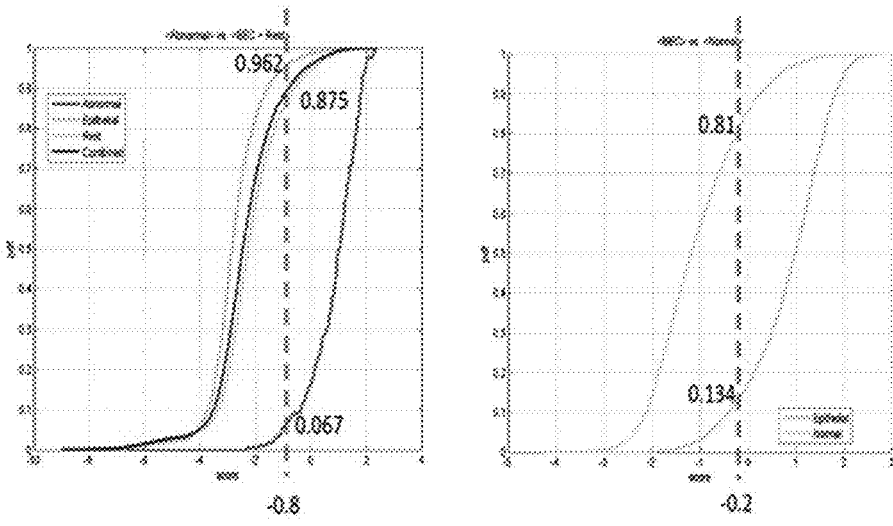
Fig. 7                    Fig. 8

AI-BASED CELL CLASSIFICATION METHOD AND SYSTEM

TECHNICAL FIELD

The present disclosure relates to a system and method for artificial-intelligence (AI)-based 2D classification of cells to prior to 3D analysis to detect cells indicative of cancer or with features of a normal bronchial epithelial cell (BEC), as well as a method of training a 2D cell classifier for use in an AI-based cell classification system and method.

BACKGROUND

Lung cancer is the most lethal cancer in the United States and over 31 million patients are at a high risk of developing lung cancer. Early detection is the most reliable means of reducing lung cancer deaths, but many detection methods have poor sensitivity and specificity, leading to missed diagnoses and, as a result, higher death rates, as well as increased costs and needless suffering caused by invasive procedures.

BRIEF SUMMARY

The present disclosure provides an artificial intelligence (AI)-based cell classification method comprising: a) generating, by an optical tomography system, a representative 2D image of a cell from a patient sample comprising a plurality of cells; b) evaluating the representative 2D image using an abnormal cell 2D classifier to determine if the cell has abnormal features; c) evaluating the representative 2D image using a BEC 2D classifier to determine if the cell has BEC-like features; and d) generating, by the optical tomography system, a 3D image of the cell if the cell is determined to have abnormal features or to have BEC-like features.

The method may further include one or more of the following additional features, in any combinations:

a 3D image of the cell is not generated if the cell is determined to not have abnormal features and to not have BEC-like features;

e) repeating a) to d) for a subset of cells within the plurality of cells to generate patient sample data that reflects a total number of enumerated analyzed cells having abnormal features, a total number of enumerated analyzed cells having BEC-like features, or a total number of enumerated analyzed cells;

f) comparing the total number of enumerated analyzed cells having BEC-like features to a threshold value to determine if the total number of enumerated analyzed cells having BEC-like feature is adequate for an accurate assay because the total number is at or above the threshold value, or if the total number of enumerated analyzed cells having BEC-like features is inadequate for an accurate assay because the total number is below the threshold value;

repeating a) to f) until the total number of enumerated analyzed cells having BEC-like features is adequate to detect the presence of cells indicative of lung cancer in the patient sample with a pre-selected accuracy;

the threshold value is pre-selected by the number of enumerated cells having BEC-like features is statistically likely to detect the presence of cells indicative of lung cancer in the patient sample with the pre-selected accuracy;

the threshold value is in a range of 250 to 2500 enumerated cells with BEC-like features, 400 to 1900 enumerated cells with BEC-like features, 600 to 1800 enumerated cells with BEC-like features, 800 to 1700 enumerated cells with BEC-like features, 1000 to 1600 enumerated cells with BEC-like features, 1200 to 1600 enumerated cells with BEC-like features, or 1300 to 1500 enumerated cells with BEC-like features;

the threshold value is at least 250 enumerated cells with BEC-like features, at least 400 enumerated cells with BEC-like features, at least 500 enumerated cells with BEC-like features, at least 600 enumerated cells with BEC-like features, at least 700 enumerated cells with BEC-like features, at least 800 enumerated cells with BEC-like features, at least 900 enumerated cells with BEC-like features, at least 1000 enumerated cells with BEC-like features, at least 1100 enumerated cells with BEC-like features, at least 1200 enumerated cells with BEC-like features, at least 1300 enumerated cells with BEC-like features, at least 1400 enumerated cells with BEC-like features, at least 1500 enumerated cells with BEC-like features, at least 2000 enumerated cells with BEC-like features, or at least 2500 enumerated cells with BEC-like features;

the method has a pre-selected 2D abnormal cell sensitivity value of at least 90%;

the method has a pre-selected 2D abnormal cell specificity value of at least 65%;

the method has a pre-selected 2D BEC sensitivity value of at least 85%;

the patient sample is obtained from a sputum specimen;

the patient sample is obtained by isolating and preserving a plurality of cells from the sputum specimen; the patient sample comprises abnormal cells, BECs, squamous cells, monocytes, lymphocytes, polymorphonuclear leukocytes, other white blood cells, debris, cell fragments, cell clusters and any combinations thereof;

abnormal cells are selected from a group consisting of cells exhibiting atypia, dysplastic cells, pre-cancerous cells, pleomorphic parakeratosis, type II pneumocyte abnormal squamous cells, adenocarcinoma cells, bronchioloalveolar carcinoma cells, abnormal neuroendocrine cells, small cell carcinoma cells, non-small cell carcinoma cells, tumor cells, neoplastic cells, bronchioloalveolar carcinoma cells, and any combination thereof;

prior to a), pre-processing the patient sample to stain the plurality of cells with an agent that facilitates generating the representative 2D image, evaluating the representative 2D image using the abnormal cell 2D classifier, or evaluating the representative 2D image using the BEC 2D classifier;

prior to a), enriching the patient sample for BECs or cells likely to be indicative of cancer;

prior to a), i) embedding the patient sample in an optical medium and injecting the optical medium with embedded sample into a capillary tube; and ii) loading the capillary tube into the optical tomography system so that the capillary tube is between an illumination source and objective lens of the optical tomography system;

wherein generating, by the optical tomography system, the 2D image of the cell comprises the optical tomography system sweeping a focal plane of the optical tomography system in 1 μm steps across a single cell to generate a single-plane 2D image of the single cell at each step, compiling a set of single-plane 2D images of the single cell, and filtering the set of single-plane 2D images of the single cell to generate the representative 2D image of the cell;

wherein the representative 2D image of the cell is an image of a central portion of the cell;

wherein evaluating the representative 2D image using an abnormal cell 2D classifier and evaluating the representative 2D image using a BEC 2D classifier both comprise determining values for a plurality of cell feature measurements;

wherein the cell feature measurements comprise object shape features, cell-shape features, cytoplasm features, cell nucleoli features, distribution of chromatin, nuclear-size features, nuclear-texture features, other morphometric elements, or any combination thereof.

The present disclosure also provides a method of training an AI-based cell classification system comprising: a) operating an optical tomography system to generate representative 2D images of cells; b) designating a known identifier for each of a plurality of the cells using the representative 2D image of such cell and a known cell identification method, wherein the known identifier is i) abnormal or having abnormal features; ii) BEC or having BEC-like features, or iii) normal or non-BEC or not having abnormal features or BEC-like features; c) computing a plurality of cell feature measurements for each of the plurality of cells from the representative 2D image of such cell; d) performing a regression between the cell feature measurements and the known identifier of each cell to designate an abnormal 2D cell classification score and a BEC 2D cell classification score for each cell; e) designating a test identifier for each cell of i) having abnormal features; ii) having BEC-like features, or iii) not having abnormal features or BEC-like features based on the abnormal 2D cell classification score and the BEC 2D classification score the cell; f) comparing the respective test identifiers to the known identifiers for each cell to calculate accuracy of the abnormal cell 2D classifier and the BEC 2D classifier.

The method may further include one or more of the following additional features, in any combinations:

comparing the accuracy of both of the 2D cell classifiers to pre-selected accuracy requirements and, if the pre-selected accuracy requirements are met by a 2D cell classifier, designating the 2D cell classifier as trained;

comparing the accuracy of both of the 2D cell classifiers to pre-selected accuracy requirements and, if the pre-selected accuracy requirements are not met by a 2D cell classifier, adjusting a parameter of the regression for the affected 2D cell classifier and repeating steps d)-f);

the pre-selected accuracy requirement is a 2D abnormal cell sensitivity value of at least 90%;

the pre-selected accuracy requirement is a 2D abnormal cell specificity value of at least 65%;

the pre-selected accuracy requirement is a 2D BEC sensitivity value of at least 85%;

the pre-selected accuracy requirement is a 2D BEC specificity value for of at least 60%;

the regression comprises Adaptively Boosted Logistic Regression, Random Forest, Decision Trees, or any combination thereof;

the known cell-identification method comprises cytological analysis and classification by a pathologist;

generating 3D images of a plurality of the cells and using the 3D images in the known cell-identification method;

the cell feature measurements comprise object shape features, cell-shape features, cytoplasm features, cell nucleoli features, distribution of chromatin, nuclear-size features, nuclear-texture features, other morphometric elements, or any combination thereof.

In addition the training method may be used to train the AI and described above or otherwise herein.

The disclosure further provides a cell classification system comprising: an optical tomography system operable to: generate a representative 2D image of a cell from a patient sample; and generate a 3D image of the cell if the cell has abnormal features or BEC-like features; and a processor operable to: compare the representative 2D image of the cell to an abnormal cell 2D classifier to determine if the cell has abnormal features; and compare the representative 2D image of the cell to a BEC 2D classifier to determine if the cell has BEC-like features.

In some embodiments, the system may be used in either the cell classification method or the training method described above or otherwise herein, or in both.

DESCRIPTION OF THE DRAWINGS

The disclosure may be better understood through reference to the following detailed description in conjunction with the drawings, which are provided as examples only, in which like elements are indicated by letters (e.g., $40a$, $40b$, $40c$), and in which:

FIG. 5 is a flow chart of a 2D classifier training method of the present disclosure;

FIG. 6 is an example 2D section of a 3D image of cells that may be obtained using an optical tomography system of the present disclosure;

FIG. 7 is a Cumulative Probability Density Curve (CDF) plot, for example abnormal cell 2D classifier results according to the present disclosure, in which the green dashed line indicates the threshold for classifier operation, the red line shows the trend for cells classified as having abnormal features ("abnormal"), the green line shows the trend for cells classified as having BEC-like features ("epithelial"), the light blue line shows the trend for miscellaneous cells ("rest"), and the dark blue line shows the trend for cells having BEC-like features and miscellaneous cells ("combined");

FIG. 8 is a CDF plot, for example BEC 2D classifier results according to the present disclosure, in which the green dashed line indicates the threshold for classifier operation, the green line shows the trend for cells classified as having BEC-like features, and the light blue line shows the trend for miscellaneous cells (normal).

DETAILED DESCRIPTION

Figure 1:
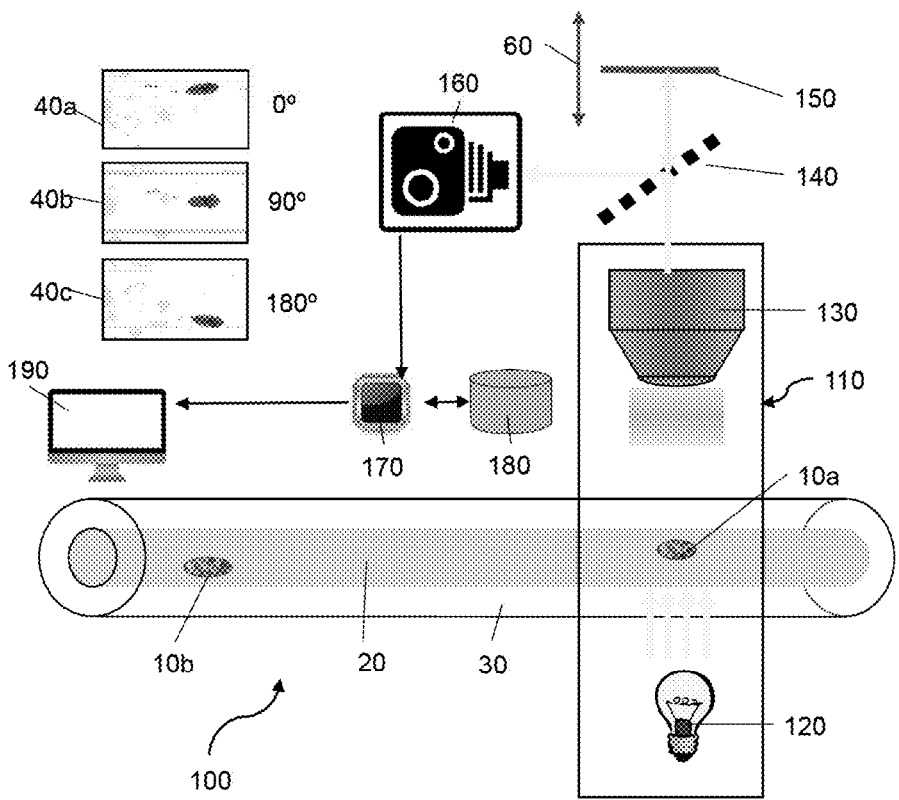
FIG. 1 is a schematic representation of an optical tomography system that may be used in the present disclosure.

The following description, along with the accompanying drawings, sets forth certain specific details to provide a thorough understanding of various disclosed embodiments. However, one skilled in the relevant art will recognize that the disclosed embodiments may be practiced in various combinations, without one or more of these specific details, or with other methods, components, devices, materials, etc. In other instances, well-known structures or components associated with the environment of the present disclosure have not been shown or described to avoid unnecessarily obscuring descriptions of the embodiments. Additionally, the various embodiments may be methods, systems, or devices.

The present disclosure relates to an AI-based cell classification method and system, which may be used to detect cells indicative of cancer among a plurality of cells in a lung-related patient sample, such as sputum. The cells indicative of cancer may be cancerous, but they may also include non-cancerous cells having abnormal features. In some embodiments, a sample may be designated as containing cells indicative of cancer (and thus positive for lung cancer) based solely on the detection of non-cancerous cells having abnormal features. When a sample is designated as containing cells indicative of cancer, the patient may be referred for further testing.

The system and method use optical tomography, such as current optical tomography systems, to detect cells and generate 3D images of the cells. However, unlike existing optical tomography systems and methods, the system and method of the present disclosure, prior to generating a 3D image of a cell, first generate a representative 2D image of the cell and analyze the representative 2D image using AI-based 2D cell classifiers to determine if a 3D image should be generated. Patient samples contain a substantial number of diverse cells that are not likely indicative of lung cancer and, therefore, are not useful in detecting lung cancer. A 3D image of such cells is not needed, and generating it is a waste of resources. Avoiding unnecessary 3D imaging of cells that are not useful in detecting lung cancer allows for more efficient sample processing.

The disclosure also provides a method of training the AI of a 2D cell classifier for use in an AI-based cell classification system or method using cells having known identifiers.

In some embodiments, the lung cancer may be non-small cell lung cancer (NSCLC), particularly squamous carcinoma and adenocarcinoma. In some embodiments, the lung cancer may be small cell lung cancer (SCLC).

The term "cancer" refers to a hyperproliferation of cells that results in unregulated growth, lack of differentiation, local tissue invasion, or metastasis.

In some embodiments, cells having abnormal features may include cells exhibiting atypia, dysplastic cells, precancerous cells, pleomorphic parakeratosis, type II pneumocyte abnormal squamous cells, adenocarcinoma cells, bronchioloalveolar carcinoma cells, abnormal neuroendocrine cells, small cell carcinoma cells, non-small cell carcinoma cells, tumor cells, neoplastic cells, bronchioloalveolar carcinoma cells, and any combination thereof.

In some embodiments, cells having BEC-like features may include cells that typically line the airway lumen in the lungs of a patient.

In some embodiments, the optical tomography system may be a CELL-CT® system (VisionGate, Inc., Washington, USA).

AI-Based Cell Classification System

Figure 2:
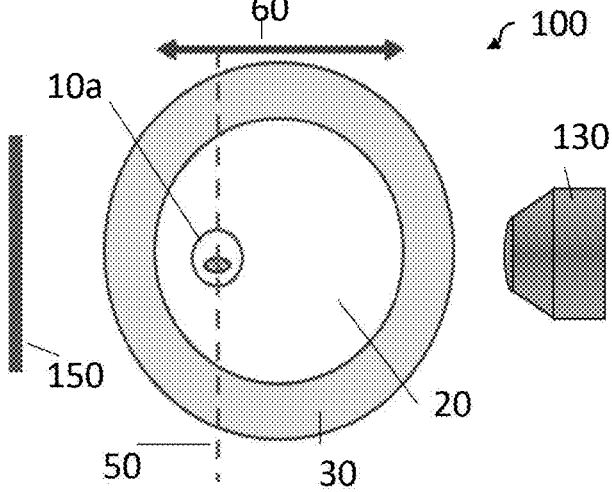
FIG. 2 is a schematic representation of the optical tomography system as operated to acquire a plurality of 2D images of a cell that may be used in the present disclosure.

Referring now to FIG. 1 and FIG. 2, an AI-based cell classification system of the present disclosure may include, or an AI-based cell classification method of the present disclosure may be carried out using an optical tomography system 100, which may be used to produce both 3D images and 2D images of a cell 10 (such as cell 10a or cell 10b). Although the operation of the optical tomography system is described for acquiring images of one cell 10, in a volume of optical medium in the optical path of a high-magnification microscope, images of multiple cells 10 within the same volume of optical medium may be acquired.

The optical tomography system 100 may include a cell imaging system 110, which includes an illumination source 120 optically coupled to an objective lens 130, such that illumination passes through the micro-capillary tube 30 and any intervening cell 10 before reaching the objective lens 130. The illumination then passes through the objective lens 130 to a beam-splitter 140, which causes part of the illumination to be deflected to a mirror 150 and reflected back to the beam-splitter 140 before being transmitted to a high-speed camera 160, and another part of the illumination to be transmitted directly through the beam-splitter 140 to the high-speed camera 160, to generate pseudo-projection images 40 of the cell 10 contained in an optical medium 20 in a micro-capillary tube 30. During 3D imaging, at least one pseudo-projection image 40 of the cell 10 is generated by scanning the volume occupied by the cell 10 by vibrating the mirror 150 in direction 60 (typically using an actuator, such as a piezo-electric motor, not shown), thus sweeping the plane of focus 50 through the cell 10 and then integrating the image to create the pseudo-projection image from a single perspective. Additional pseudo-projection images are obtained by rotating the micro-capillary tube 30. The pseudo-projection images are each a single image that represents a sampled volume that has an extent greater than the depth of field of the objective lens 130. The high-speed camera 160 generates, for each cell 10, a plurality of pseudo-projection images 40 that correspond to a plurality of axial micro-capillary tube rotation positions, examples of which are illustrated as 40a, 40b, and 40c in FIG. 1. In some embodiments, 500 pseudo projection images are generated as the micro-capillary tube 30 is rotated through 360°.

In some embodiments, optical tomography system 100 is communicatively coupled to a processor 170 operable to receive the plurality of pseudo-projection images 40 from the high-speed camera 160 and use the pseudo-projection images 40 to generate a 3D image (not shown) of the cell 10. Images before or after manipulation by the processor 170 may be stored in communicatively coupled memory 180. The processor 170 may send data regarding the cell 10, or data relating to or derived from a plurality of cells 10 contained in a patient sample to a communicatively coupled output 190. Data sent to the output 190 may include 2D or 3D images of one or more cells 10, or a summary of cells in a patient sample analyzed by the optical tomography system 100, such as a graph or a table, an index, such as an abnormality index, reflecting the likelihood that the patient has or is at high risk for developing lung cancer, or even a simple indication that the sample is positive for cells indicative of lung cancer.

In embodiments disclosed herein, the optical tomography system 100 may also be operated to generate a representative 2D image of the cell 10. In such embodiments, the objective lens 130 has a focal plane 50 that moves as the objective lens 130 sweeps across the micro-capillary tube 30 and any cell 10 in a back-and-forth direction 60 to produce a plurality of 2D images (not shown). This method of generating 2D images by moving the objective lens 130 is different than the method of producing 3D images using pseudo-projection images that are generated by vibrating the mirror 150. The processor 170 is operable to receive the plurality of 2D images and determine a representative 2D image of the cell 10. In some embodiments, the representative 2D image of the cell 10 is an image of the central portion, such as the center) of the cell. The processor 170 is then further operable to perform AI-based cell classification of the representative 2D image using 2D cell classifiers as described herein to determine if the cell 10 has abnormal features or BEC-like features, or does not have abnormal features or BEC-like features. Only when the cell 10 is determined to have abnormal features or to have BEC-like features does the processor 170 direct the cell imaging system 110 to generate pseudo-projection images 40 of the cell 10.

A substantial number of cells 10 in a patient sputum sample or other samples are not likely to be indicative of lung cancer, such that producing a 3D image of these cells is not useful in detecting lung cancer. Many of these cells do not have the morphology of normal or abnormal cells of the bronchial epithelium so they may be eliminated using only a 2D image. It is difficult to remove such cells from the patient sample prior to AI-based cell classification, so in prior cell classification methods these are simply imaged along with cells that are likely to be indicative of lung cancer. The capability of using 2D images to first assess whether a cell is likely to be indicative of lung cancer before capturing pseudo-projection images 40 allows the AI-based cell classification to focus on cells 10 that provide meaningful information while not wasting processing and analysis time on cells that are not useful in detecting lung cancer.

In some embodiments, the cell imaging system 110 includes the illumination source 120, the objective lens 130, the beam-splitter 140, mirror 150, and the high-speed camera 160.

In some embodiments, the optical tomography system 100 further includes the processor 170, any communicatively coupled memory 180, and the communicatively coupled output 190.

In certain embodiments, the optical tomography system 100 further includes the micro-capillary tube 30, the optical medium 20, or one or more cells 10, but in other embodiments, the optical tomography system 100 does not include one or more of these potential components, although they may be supplied for operation of the system.

In certain embodiments, the AI-based cell classification system 100 is operable to generate images in at least two distinct modes. One mode includes a cell search mode, during which 2D images of a cell 10 are generated and processed to generate a representative 2D image, which is then used to determine whether the cell 10 has abnormal features or BEC-like features. 2D images in this mode are generated by moving the objective lens 130 in direction 60 to sweep the focal plane 50 through the cell. A second mode includes a projection image capture mode, during which pseudo-projection images 40 are generated and used to produce a 3D image of the cell 10 if the cell 10 has been determined to have abnormal features or BEC-like features during the cell search mode. 3D images in this mode are generated by vibrating the mirror 150 in direction 60 to create the pseudo-projection images 40.

Lung Cancer Detection Methods

Figure 3:
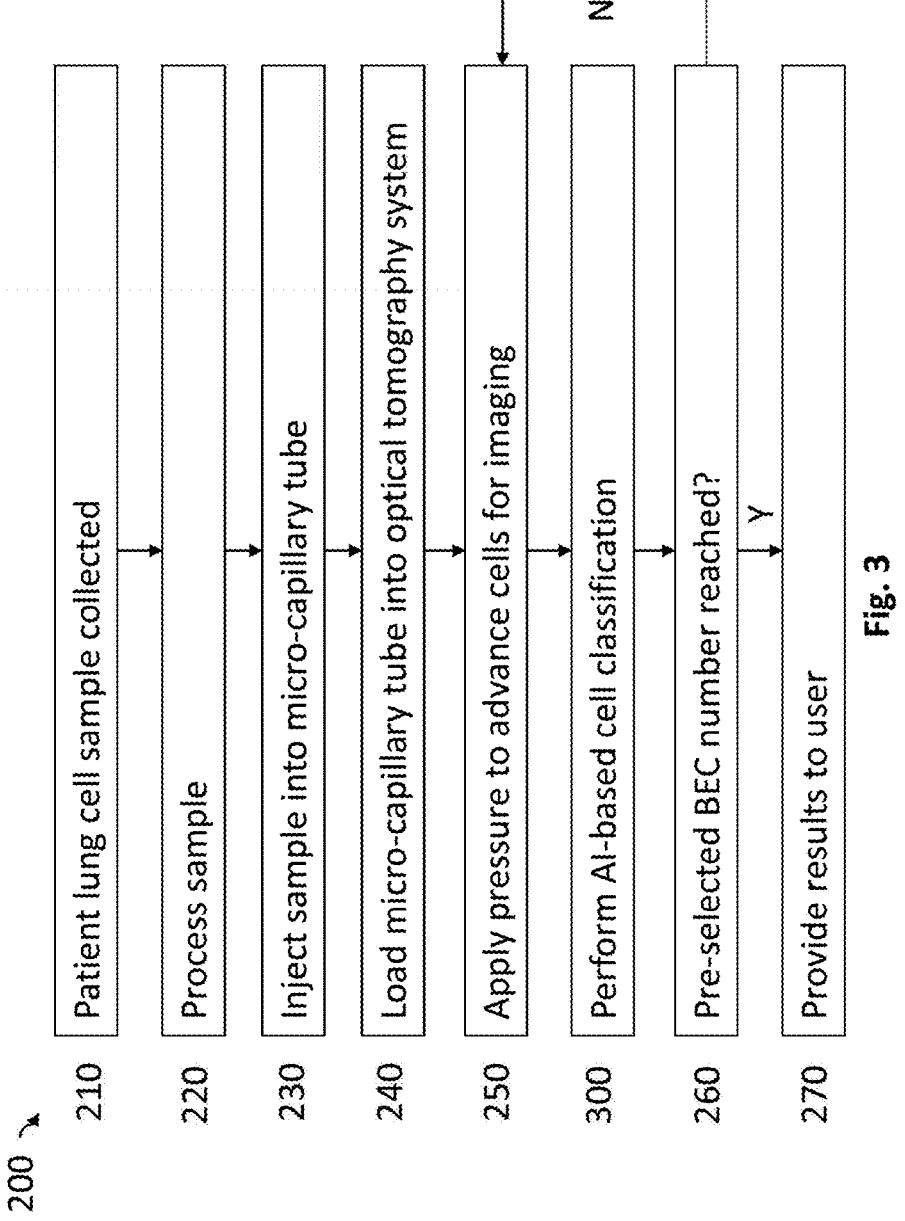
FIG. 3 is a flow chart for a lung cancer detection method of the present disclosure.
Figure 4:
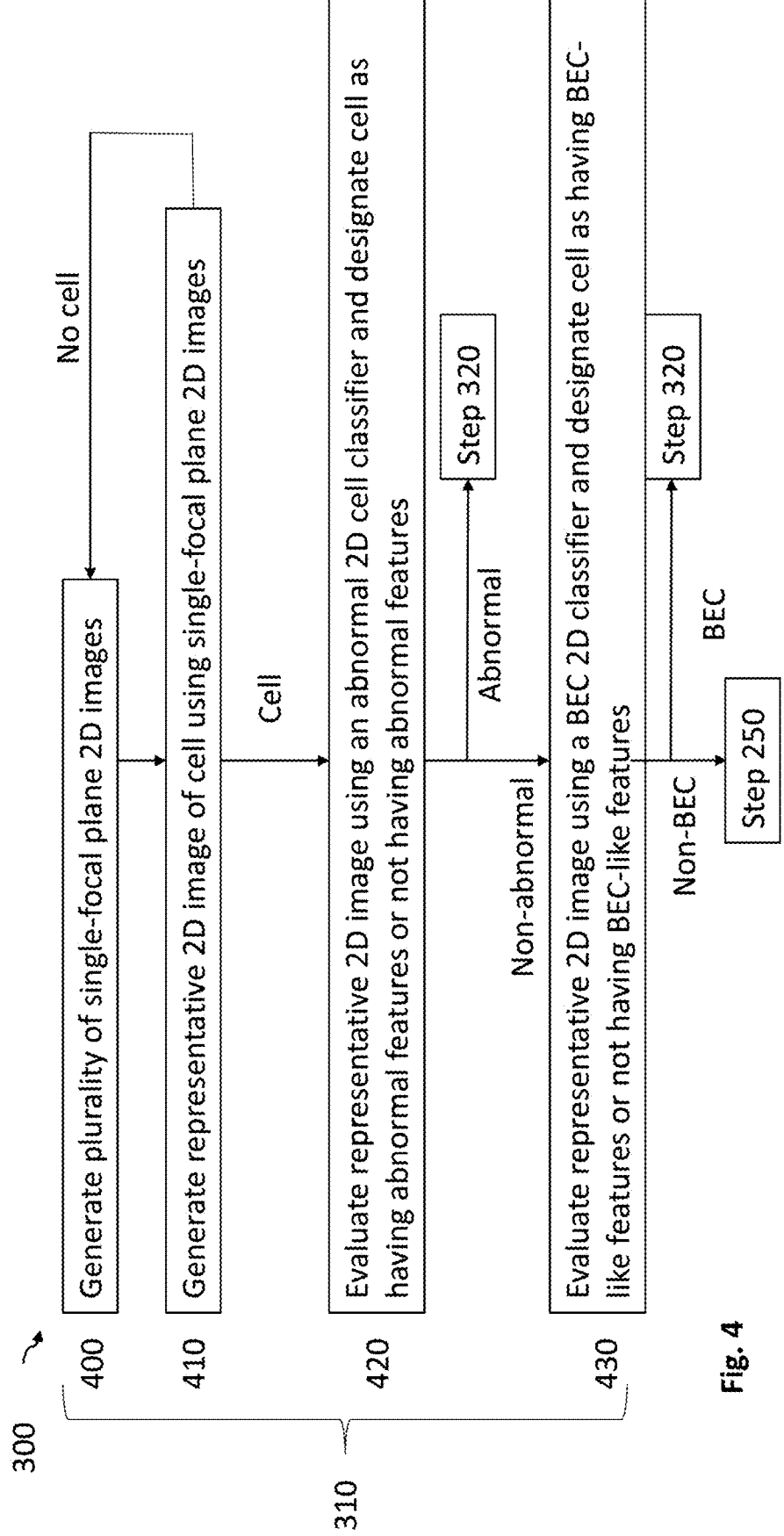
FIG. 4 is a flow chart of an AI-based cell classification method of the present disclosure for use in the lung cancer detection method of FIG. 3.
Figure 4:
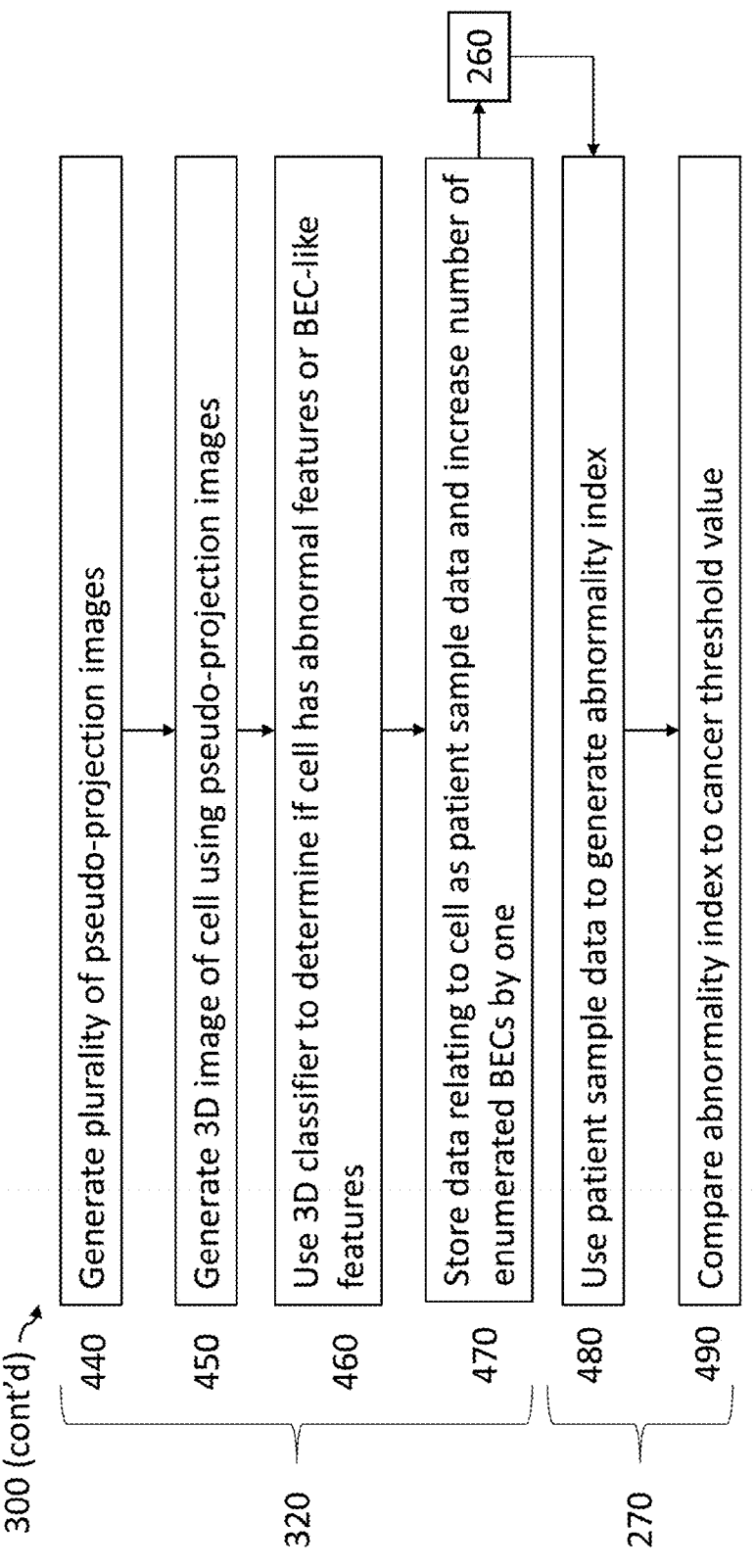

FIG. 3 and FIG. 4 describe a lung cancer detection method 200, which may be performed using an optical tomography system, such as the optical tomography system 100. Elements of the optical tomography system 100 are referenced in this description of the lung cancer detection method 200 as examples. Similar components of different optical tomography systems may also be used in connection with the lung cancer detection method 200.

The lung cancer detection method 200 includes a step 210 in which a lung cell sample is collected from a patient. For example, the lung cell sample may be sputum, although other sample types, such as samples obtained by bronchoalveolar lavage (BAL), nasal swab, or biopsy may also be used. In some embodiments, particularly for the detection of other cancers or abnormal cells, samples may include urine or blood.

Samples may undergo an AI-based cell classification method 300 at any time during which cells are not to have degraded to the point where limited cellular content remains. The duration of such time may depend on the storage conditions, e.g., whether the sample is refrigerated or how or if the sample is processed. In some embodiments, the sample may undergo the AI-based cell classification method 300 within 30 minutes, one hour, two hours, 6 hours, 12 hours, one day, two days, one week, or two weeks of collection.

Particularly in the case of sputum samples, the patient sample may include many cell types that are not likely to be indicative of lung cancer, such as white blood cells, including polymorphonuclear leukocytes, monocytes, and lymphocytes, cell clusters, oral squamous cells, and squamous intermediate cells (pictured in FIG. 6, upper panel). The sample also typically will contain a substantial amount of non-cellular debris or cell fragments.

In some embodiments, the sample contains abnormal cells, BECs, squamous cells, monocytes, lymphocytes, polymorphonuclear leukocytes, other white blood cells, debris, cell fragments, cell clusters and any combinations thereof.

In step 220 the sample is processed for analysis. Processing may optionally include staining to render any of the plurality of cells 10 or any features, such as the nucleus of any of the plurality of cells 10, easier to detect using the optical tomography system 100, or otherwise staining or treating the cells with an agent that facilitates generating the representative 2D image, evaluating the representative 2D image using an abnormal cell 2D classifier, evaluating the representative 2D image using a BEC 2D classifier, generating a 3D image of the cell, or analyzing a 3D image of the cell. In specific embodiments, the cells may be stained with hematoxylin.

Processing may optionally include, alone or in combination with staining, enrichment of the sample for cells of interest. For example, in some embodiments, the sample is enriched for BECs.

In one embodiment, the sample may be enriched for BECs by staining cytoskeleton proteins and using fluorescently activated cell sorting (FACS)-based enrichment.

In one embodiment, BEC enrichment may include treating the sample with at least one antibody, and typically a plurality of antibodies, having fluorescent conjugates that may be used for FACS-based enrichment. In particular, the antibodies may bind to BECs or they may bind contaminating inflammatory cells, such a neutrophils and macrophages. Antibodies that bind contaminating inflammatory cells may include anti-CD45 antibodies. In some embodiments, the sample is treated with a combination of antibodies that bind to BECs and antibodies that bind contaminating inflammatory cells, with the antibodies having distinct fluorescent conjugates.

In one embodiment, the cells may be stained with 4',6-diamidino-2-phenylindole (DAPI) alone or in combination with antibodies for FACS-based cell enrichment purposes as well.

Cells may be enriched by FACS in which gating is used to exclude DAPI-positive materials (which tend to be doublet cells or debris), high side-scatter objects, objects bound by anti-inflammatory cell antibodies, or any combinations thereof. Cells may also be enriched by FACS in which gating is used to select cells that are bound by anti-BEC antibodies.

In some embodiments, both exclusive and inclusive gating may be used and may be implemented concurrently or in series.

Following any optional staining or enrichment, the sample processing 220 includes placing the cells 10 contained in the sample in an optical medium 20.

The optical medium 20 may be any medium reasonably expected to maintain the cells 10 intact during the expected duration of time prior to and during the AI-based cell classification 300. The optical medium 20 may also have a viscosity that allows movement of the optical medium 20 through a micro-capillary tube 30. The optical medium 20 may also not interfere with image generation by the optical tomography system 100. In particular, the optical medium may have an optical index that matches the optical index of other components of the optical tomography system 100 and the micro-capillary tube 30 through which light passes during image acquisition. Typically the optical tomography system 100 components through which light passes and the micro-capillary tube 30 also have a matching index. For optimal optical tomography operation, any changes in light movement should be due to encountering the object to be imaged, not changes in the optical index of other components or objects in the light path.

In the step 230, the optical medium 20 containing a plurality of cells 10 from the patient sample is injected into a micro-capillary tube 30. In some embodiments, the micro-capillary tube 30 may have an outer diameter of 500 μm or less, for example, between 30 μm and 500 μm. In some embodiments, the micro-capillary tube 30 may have an inner diameter of 400 μm or less, for example, between 30 μm and 400 μM, such as 50 μm. In one embodiment, the entire portion of the patient sample to be analyzed is placed in one micro-capillary tube 30. In another embodiment, the portion of the patient sample to be analyzed is placed in a plurality of micro-capillary tubes 30, which may undergo the AI-based cell classification method 300 sequentially. In still another embodiment, the sample may be pumped through the micro-capillary tube 30 from a sample reservoir.

In the step 240, the micro-capillary tube 30 is loaded into the optical tomography system 100, so that the micro-capillary tube 30 is between the illumination source 120, and the objective lens 130.

In step 250 the optical medium 20 and any cells 10 contained within it are advanced into (prior to the initial step 240) or through the micro-capillary tube 30 by applying pressure at one end of the micro-capillary tube, such that a different volume of the optical medium 20 carrying a different portion of the patient sample is in the optical path of the optical tomography system 100, between the illumination source 120 and the objective lens 130. In some embodiments, a plunger (not shown) is used to advance the optical medium 20. For instance a plunger may be applied to a reservoir (not shown) of the optical medium 20 and patient sample that is connected to the micro-capillary tube 30, forcing additional optical medium 20 from the reservoir into the micro-capillary tube 30

Next, the method proceeds to the AI-based cell classification 300, which includes a cell search mode 310 and a projection image capture mode 320, both of which are described in further detail in FIG. 4.

In the cell search mode 310, the optical tomography system 100 generates 2D images of a cell 10 that are further processed to generate a representative 2D image that is used to determine whether the cell 10 has abnormal features or BEC-like features. In some embodiments, an algorithm selects an image of a central portion, such as the center, of the cell 10 as the representative 2D image. In some embodiments, in the cell search mode 310, the optical tomography system 100 sweeps the focal plane 50 through the cell 10 in the direction 60 at 1 μm intervals to capture a series of 2D images. Multiple cells 10 may be identified in the same volume of optical medium 20 in the optical path of the optical tomography system 100.

In the projection image capture mode 320, each of cells 10 identified as having abnormal features or having BEC-like features is further imaged to generate a plurality of pseudo-projection images 40, which are used to generate a 3D image of the cell 10.

In step 260, it is determined whether a pre-selected number of cells having BEC-like features have been 3D imaged. If the pre-selected number has been reached, the process moves on to step 270. Otherwise, the process returns to step 250 and advances the sample in the micro-capillary tube.

In step 270, images of cells selected for 3D imaging are provided to a user, for example, using the output 190. Results may include results specific for an individual cell 10, such as the 3D image of cell 10. AI-based cell classification results may also include data based upon the analysis of all or a portion of the patient sample or plurality of cells 10, such as an abnormality index and/or a cancer threshold value as explained further in FIG. 4. For example, the AI-based cell classification results may include a list or other indication of individual cells 10 found to have abnormal features or BEC-like features or otherwise marked according to pre-selected criteria for further review of the 3D image by the user. The AI-based cell classification results may include graphical, statistical, or numerical information, such as the number of cells detected (typically the total enumerated analyzed cells), the number of cells for which a 3D image was generated, the number of enumerated cells having abnormal features, the number of enumerated cell having BEC-like features, or the relative proportions of any of these groups of cells. The AI-based cell classification results may also contain information regarding the predicted accuracy. The AI-based cell classification results may include an index, such as an abnormality index, reflecting the likelihood that the patient has or is at high risk for developing lung cancer, or even a simple indication that the sample is positive for cells indicative of lung cancer.

Sample identification data may also be provided with the AI-based cell classification results.

Referring specifically to FIG. 4, the AI-based cell classification method 300 may include a cell search mode 310 and a projection image capture mode 320.

The cell search mode 310 may include step 400, in which the optical tomography system 100 generates a plurality of single-focal plane 2D images of a cross-sectional region of the micro-capillary tube 30, each image at a different focal plane 50 by sweeping the focal plane 50 across the micro-capillary tube (and any cell in any of the focal panes 50) back-and-forth in direction 60 by moving the objective lens 130. In one embodiment, the single-focal plane 2D images may be taken in 1 μm increments in direction 60.

In step 410, a representative 2D image of a cell 10 is generated. To do so, at least a portion of the plurality of single-focal plane 2D images are compiled and filtered by the processor 170 to determine if the 2D image contains features associated with a cell 10 or other solid object in the optical medium 20, such as being dark as compared to the optical medium 20. If the plurality of single-focal plane 2D images contain features associated with a cell 10 or other solid object, then at least a portion of the plurality of single-focal plane 2D images associated with the cell 10 (for example, all or a portion of the 2D images containing a dark region), are analyzed by the processor 170 to determine which should be designated as a representative 2D image based on pre-selected criteria. In one embodiment, the processor determines which 2D image represents a central portion, such as the center, of the cell 10. This image representing the central portion of the cell 10 is designated as the representative 2D image of the cell 10.

If a representative 2D image is generated, then the process proceeds to step 420. In some embodiments, rather than proceeding directly to step 250, the method determines if another cell 10 is present in the volume of optical medium and proceeds to conduct step 410 (and, optionally, step 400 if further 2D images are needed) for the other cell. This may be repeated for all, a set number of, or a set proportion of putative cells 10 in the volume of optical medium 20 in the optical path of the optical tomography system 100.

In step 420, the processor 170 evaluates the representative 2D image using an abnormal cell 2D classifier to determine if the cell 10 has abnormal features. The processor may use an AI-trained or implemented algorithm in step 420. The abnormal cell 2D classifier may be trained as set forth in the training method 500 herein. Specifically the abnormal cell 2D classifier may identify a plurality of features of the cell 10 and make cell feature measurements, then compare at least a subset of such cell feature measurements to trained values for cell feature measurements associated with cells having abnormal features and, optionally, also cells not having abnormal features. The cell may be identified as having abnormal features or not having abnormal features based upon the comparison. To facilitate identifying and measuring the plurality of cell features, the abnormal cell 2D classifier may segment the representative 2D image into a nucleus portion and a non-nucleus cellular portion. The cell feature measurements may include object shape features, cell-shape features, cytoplasm features, cell nucleoli features, distribution of chromatin, nuclear-size features, nuclear-texture features, other morphometric elements, or any combination thereof.

The abnormal cell 2D classifier may have a pre-selected abnormal cell 2D accuracy, typically a pre-selected abnormal cell 2D sensitivity or a pre-selected abnormal cell 2D specificity.

If the cell 10 is determined to have abnormal features in 2D, then the method may progress directly to the projection image capture mode 320 as shown. However, in some embodiments, even if the cell 10 is determined in 2D to have abnormal features, the method may still progress to step 430 (not shown) to also determine if the cell 10 has BEC-like features in 2D.

In the embodiment illustrated, if the cell 10 is determined to not have abnormal features, then the method progresses to step 430.

Next, in step 430, the processor 170 evaluates the representative 2D image using a BEC 2D classifier to determine if the cell 10 has BEC-like features. The processor may use an AI-trained or implemented algorithm in step 430. The BEC 2D classifier may be trained as set forth in the training method 500 herein. Specifically, the BEC 2D classifier may identify a plurality of features of the cell 10 and make cell feature measurements, then compare at least a set of the identified and measured cell features measurements to trained values for cell feature measurement associated with cells having BEC-like features and, optionally, also cells not having BEC-like features. The cell may be identified as having BEC-like features or not having BEC-like features based upon the comparison. The cell features and cell feature measurements may be selected from the same group set forth above for the abnormal cell 2D classifier. In some embodiments, cell features identification and measurement may be conducted separately for use with the abnormal cell 2D classifier and the BEC 2D classifier. The cell may be designated having BEC-like features or not having BEC-like features based upon the comparison.

The BEC 2D classifier may have a pre-selected 2D BEC accuracy, typically a pre-selected 2D BEC sensitivity or 2D BEC specificity.

Operating together, the abnormal cell 2D classifier and the BEC 2D classifier may have a pre-selected abnormal cell referral rate or a pre-selected BEC referral rate.

If the cell 10 is determined to have BEC-like features, then the method progresses directly to the projection image capture mode 320 as shown. If the cell 10 is determined to not have BEC-like features, then no 3D image is captured and the method progresses to step 250. In some embodiments (not shown), rather than proceeding directly to step 250, the method determines if another cell 10 is present in the volume of optical medium and proceeds to conduct steps conduct steps 410-430 (and, optionally, step 400 if further 2D images are needed) for the other cell. This may be repeated for all, a set number of, or a set proportion of putative cells 10 in the volume of optical medium 20 in the optical path of the optical tomography system 100.

In projection image capture mode 320, in step 440, the optical tomography system 100 generates a plurality of pseudo-projection images 40 by vibrating the mirror 150. These images may be taken over 360 degrees of rotation around the cell 10. However, pseudo-projection 40 may be taken over as little as 180 degrees of rotation around the cell 10.

Next, in step 450, the processor 170 uses at least a portion of the plurality of pseudo-projection images 40 to generate a 3D image of the cell 10. Typically all pseudo-projection images 40 are used to generate the 3D image of the cell 10. However, if pseudo-projection images 40 that are determined to be of poor quality or likely to contain errors, the 3D imaging of the cell may be discontinued. In addition, typically pseudo-projection images 40 that cover 360 degrees of rotation around the cell 10 are used to generate the 3D image, but pseudo-projection images that cover as little as 180 degrees of rotation around the cell 10 may be used.

In step 460, the processor 170 uses a 3D classifier to determine if the cell has abnormal features or BEC-like features. This information is used to determine if the cell is likely indicative of lung cancer. The 3D classifier may also have pre-selected accuracy values.

The process then returns to step 260 to determine if a pre-selected number of BECs have been 3D imaged. If the pre-selected number has been reached, then the process moves on to step 270, which, in some embodiments, may include steps 470 and 480.

In step 470, data relating to the cell is stored as patient sample data. Patient sample data may be used in determining an abnormality index. Patient sample data may also reflect a total number of enumerated analyzed cells having abnormal features, a total number of enumerated analyzed cells having BEC-like features, or a total number of enumerated analyzed cells and steps 410-470 and, optionally, step 400 if additional 2D images are needed, may be repeated for additional cells until a pre-selected threshold value of any or all of these total numbers is reached.

In step 480, the processor compares the total number of enumerated analyzed cells having abnormal features with the total number of enumerated analyzed cells having BEC-like features or the total number of enumerated analyzed cells to generate an abnormality index. For example, the abnormality index may be correlated with the proportions of any of these totals.

In step 490, the processor compares that abnormality index to a cancer threshold value set to correspond with the patient sample being designated positive for cells indicative of lung cancer.

The overall method 300, which includes 2D cell classification and 3D cell classification, may have a pre-selected assay accuracy, such as a pre-selected assay sensitivity or a pre-selected assay specificity. cell classification method 300 as described herein may be substantially quicker than an analogous method that does not use 2D cell classifiers and, instead, generates a 3D image of every cell or putative cell identified. In some embodiments, the method 300 may reduce cell classification time, such as for steps 400-460, by at least 25%, at least 35%, at least 40%, at least 45%, at least 50%, or in a range of 25% to 60%, 25% to 50%, 25% to 45%, 25% to 40%, 25% to 35%, 35% to 60%, 35% to 50%, 35% to 45%, 35% to 40%, 40% to 60%, 40% to 50%, 40% to 45%, 45% to 60%, or 45% to 50%.

Although, in the embodiment as described in cell classification method 300, a 3D image is not generated for cells that do not have abnormal features or BEC-like features as determined using 2D classification, in other embodiments, a 3D image may be generated for at least one cell or a plurality of cells that do not have abnormal features or BEC-like features. Such images may be used, for example, to verify performance or accuracy of the AI-based cell classification system or method and or one or both of the component 2D cell classifiers. Although generating such 3D images will increase the total cell classification time, so long as 3D images are not generated for all cells, a reduction in time should still be achieved as compared to methods in which all or nearly all cells are 3D imaged. In some embodiments, the total number of cells that do not have abnormal features or BEC-like features for which 3D images are generated may be limited to 25% or less, 20% or less, 15% or less, 10% or less, 5% or less, 1% or less, or in a range of 0.1% to 25%, 0.1% to 20%, 0.1% to 15%, 0.1% to 10%, 0.1% to 5% 0.1% to 1%, 1% to 25%, 1% to 20%, 1% to 15%, 1% to 10%, 1% to 5%, 5% to 25%, 5% to 20%, 5% to 15%, 5% to 10%, 10% to 25%, 10% to 20%, 10% to 15%, 15% to 15%, 15% to 20%, or 20% to 25% of the total number of enumerated analyzed cells having abnormal features, the total number of enumerated analyzed cells having BEC-like features, or the total number of enumerated analyzed cells. Cells that do not have abnormal features or BEC-like features that are selected for 3D imaging may be randomly selected or selected based on pre-selected criteria, such as criteria that cause a 3D image to be generated for at least one of the most common cells types in the sample.

The AI-based cell classification method 300 as described herein may also substantially reduce the number of cells for which a 3D image is generated as compared to an analogous method that does not use an abnormal cell 2D classifier and a BEC 2D classifier (collectively, 2D cell classifiers) and, instead, generates a 3D image of every cell or putative cell identified. In some embodiments, the method 300 may reduce the number of cells for which a 3D image is generated by at least 30%, at least 40%, at least 50%, at least 55%, at least 60%, or in a range of 30% to 70%, 30% to 60%, 30% to 55%, 30% to 50%, 30% to 40%, 40% to 70%, 40% to 60%, 40% to 55%, 40% to 50%, 50% to 70%, 50% to 60%, 50% to 55%, 55% to 70%, 55% to 60%, or 60% to 70%.

The abnormal cell 2D classifier, the BEC 2D classifier, and the overall AI-based cell classification method may have pre-selected accuracies.

For any assay, the "sensitivity" of the assay is defined as the percent of assayed items (such as cells or the sample as a whole) that are actually positive for a property that are also correctly identified as positive by the assay.

For any assay the "specificity" of the assay is defined as the percent of assayed items (such as cells or the sample as a whole) that are actually negative for a property that are also correctly identified as positive by the assay.

For the 2D cell classifiers used in the cell classification method 300, sensitivity tends to be a more significant measure of accuracy than specificity because only cells that are positive for abnormal features or BEC-like features are 3D imaged. Accordingly, a poor sensitivity for either 2D cell classifier can result in cells that are likely to be indicative of cancer not being 3D imaged and not included in the lung cancer test results, potentially resulting in false negatives. In contrast, if specificity is poor, then more cells will be 3D imaged than is needed, unnecessarily slowing the AI-based cell classification somewhat, but not resulting in any cells that are likely to be indicative of cancer being missed and false negatives.

In the context of the abnormal cell 2D classifier, 2D abnormal cell sensitivity is the percent of cells that are or would be determined to be abnormal using a known identification method, such as cytology (e.g. review by a pathologist), that are identified by the abnormal cell 2D classifier as having abnormal features. 2D abnormal cell specificity is the percent of cells that are or would be determined to be normal using a known identification method, such as cytology, that are identified as not having abnormal features by the abnormal cell 2D classifier.

In some embodiments, the pre-selected 2D abnormal cell sensitivity may be at least 90%, at least 95%, at least 98%, or in a range of 90% to 100%, 90% to 99.9%, 90% to 99%, 90% to 98%, 90% to 95%, 95% to 100%, 95% to 99.9%, 95% to 98%, 98% to 100%, 98% to 99.9%, or 98% to 99%.

In other embodiments, the pre-selected 2D abnormal cell specificity may be at least 65%, at least 70%, at least 75%, or in a range of 65% to 100%, 65% to 99%, 65% to 90%, 65% to 80%, 65% to 75%, 65% to 70%, 70% to 100%, 70% to 99%, 70% to 90%, 70% to 80%, 70% to 75%, 75% to 100%, 75% to 99%, 75% to 90%, or 75% to 80%.

In the context of the BEC 2D classifier, 2D BEC sensitivity is the percent of cells that are or would be determined to be BECs using a known identification method, such as cytology, that are identified as having BEC-like features by the BEC 2D classifier. 2D BEC specificity is the percent of cells that are or would be determined to not be BECs using a known identification method, such as cytology, that are identified as not having BEC-like features by the BEC 2D classifier.

In some embodiments, the pre-selected 2D BEC sensitivity may be at least 85%, at least 90%, at least 95%, or in a range of 85% to 100%, 85% to 99%, 85% to 95%, 85% to 90%, 90% to 100%, 90% to 99%, 90% to 95%, 95% to 100%, or 95% to 99%.

In some embodiments, the pre-selected 2D BEC specificity may be at least 60%, at least 65%, at least 70%, or in a range of 60% to 100%, 60% to 90%, 60% to 80%, 60% to 70%, 65% to 100%, 65% to 90%, 65% to 80%, 65% to 70%, 70% to 100%, 70% to 90%, or 70% to 80%.

In the context of AI-based 2D cell classification using both 2D cell classifiers, an abnormal cell referral rate may also be calculated. The abnormal cell referral rate is the percent of cells that are or would be determined to be abnormal using a known identification method, such as cytology, that are identified as having abnormal features or as having BEC-like features and are, therefore, 3D imaged. The abnormal cell referral rate may be higher than the 2D abnormal cell sensitivity because cells that are abnormal, but that are not identified as having abnormal features, may still be identified as having BEC-like features and subject to 3D imaging for that reason.

In some embodiments, the pre-selected abnormal cell referral rate may be at least 70%, at least 80%, at least 85%, at least 90%, at least 95%, at least 98%, at least 99%, or in a range of 70% to 99.9%, 80% to 99.9%, 85% to 99.9%, 90% to 99.9%, 95% to 99.9%, 98% to 99.9%, 99% to 99.9%, 70% to 99%, 80% to 99%, 85% to 99%, 90% to 99%, 95% to 99%, 98% to 99%, 70% to 98%, 80% to 98%, 85% to 98%, 90% to 98%, 95% to 98%, 70% to 95%, 80% to 95%, 85% to 95%, 90% to 95%, 70% to 90%, 80% to 90%, 85% to 90%, 70% to 85%, 80% to 85%, or 70% to 80%.

In the context of AI-based 2D cell classification using the abnormal cell 2D classifier alone or in combination with the BEC 2D classifier, an abnormal cell true positive referral rate may also be calculated. The abnormal cell true positive referral rate is the percent of cells that are or would be determined to be abnormal using a known identification method, such as cytology, that are identified as having abnormal features by the abnormal cell 2D classifier. The abnormal cell true positive referral rate may, in practice, be less significant than the abnormal cell referral rate because accurate results can be obtained regardless of why abnormal cells were 3D imaged. In some embodiments, the abnormal cell true positive referral rate may be at least 60%, at least 70%, at least 80%, at least 90%, or in a range of 60% to 99.9%, 70% to 99.9%, 80% to 99.9%, 90% to 99.9%, 60% to 99%, 70% to 99%, 80% to 99%, 90% to 99%, 60% to 90%, 70% to 90%, 80% to 90%, 60% to 80%, 70% to 80%, or 60% to 70%.

In the context of AI-based 2D cell classification using both 2D cell classifiers, a BEC referral rate may also be calculated and considered in determining accuracy. The BEC referral rate is the percent of cells that are or would be determined to be BECs using a known identification method, such as cytology, that are identified as having abnormal features or BEC-like features and are, therefore, 3D imaged. The BEC referral rate may be higher than the BEC 2D classifier sensitivity because BECs that are not identified as having BEC-like features may still be identified as having abnormal features and subject to 3D imaging for that reason. A given number of BECs is typically imaged in order to ensure accuracy of a lung cancer assay of this type, so the number of BECs actually 3D imaged can influence how long it takes to conduct a lung cancer assay with a given patient sample or whether the sample is deemed adequate for accurate results.

In some embodiments, the pre-selected BEC referral rate may be at least 70%, at least 75%, at least 80%, at least 85%, at least 90%, at least 91%, at least 95%, or in a range of 70% to 99.9%, 75% to 99.9%, 80% to 99.9%, 85% to 99.9%, 90% to 99.9%, 91% to 99.9%, 95% to 99.9%. 70% to 99%, 75% to 99%, 80% to 99%, 85% to 99%, 90% to 99%, 91% to 99%, 95% to 99%, 70% to 95%, 75% to 95%, 80% to 95%, 85% to 95%, 90% to 95%, 70% to 91%, 75% to 91%, 80% to 91%, 85% to 91%, 90% to 91%, 70% to 90%, 75% to 90%, 80% to 90%, 85% to 90%, 70% to 85%, 75% to 85%, or 80% to 85%.

In the context of AI-based 2D cell classification using the BEC 2D classifier alone or in combination with the abnormal cell 2D classifier, a BEC true positive referral rate may also be calculated. The BEC true positive referral rate is the percent of cells that are or would be determined to be BECs using a known identification method, such as cytology, that are identified as having BEC-like features by the BEC 2D classifier. The BEC true positive referral rate may, in practice, be less significant than the BEC referral rate because accurate results can be obtained regardless of why BECS were 3D imaged. In some embodiments, the BEC true positive referral rate may be at least 50%, at least 60%, at least 70%, at least 80%, at least 90%, or in a range of 50% to 99.9%, 60% to 99.9%, 70% to 99.9%, 80% to 99.9%, 90% to 99.9%, 50% to 99%, 60% to 99%, 70% to 99%, 80% to 99%, 90% to 99%, 50% to 90%, 60% to 90%, 70% to 90%, 80% to 90%, 50% to 80%, 60% to 80%, 70% to 80%, 50% to 70%, 60% to 70%, or 50% to 60%.

The AI-based cell classification method 300 may also have a pre-selected 2D rejection rate. The 2D rejection rate is the proportion of the total number of enumerated analyzed cells that are identified as not having abnormal features or BEC-like features and, therefore, are not 3D imaged. In some embodiments, the 2D rejection rate may be 70% or less, 60% or less, 55% or less, 50% or less, or in a range of 0% to 70%, 1% to 70%, 10% to 70%, 25% to 70%, 40% to 70%, 50% to 70%, 55% to 70%, 60% to 70%, 0% to 60%, 1% to 60%, 10% to 60%, 25% to 60%, 40% to 60%, 50% to 60%, 55% to 60%, 0% to 55%, 1% to 55%, 10% to 55%, 25% to 55%, 40% to 55%, 50% to 55%, 0% to 50%, 1% to 50%, 10% to 50%, 25% to 50%, or 40% to 50%.

Accuracy values may be calculated for the 3D classifier as well. Specifically, the AI-based cell classification method may have a 3D abnormal cell sensitivity that is the percent of cells that are or would be determined to be abnormal using a known identification method, such as cytology (e.g. review by a pathologist), that are identified by the 3D classifier as abnormal (or positive as indicative of lung cancer). When calculating the 3D abnormal cell sensitivity, the number of false negative cells not referred for 3D imaging by the 2D classifiers must be subtracted from the known abnormal cell total, as the 3D classifier did not have the opportunity to classify such cells as abnormal. A pre-selected minimum 3D abnormal cell sensitivity helps avoid false negative test results. Similar calculations may be made for other accuracy parameters of the 3D cell classifier.

The lung cancer detection method 200 also has pre-selected lung cancer accuracy parameters for the lung cancer test as a whole. The lung cancer sensitivity is the percent of patients who actually have lung cancer who are identified as having lung cancer by the lung cancer detection method (a positive rest result). The AI-based cell classification method 300 also has pre-selected assay accuracy parameters. In some embodiments, the may be the same as the lung cancer accuracy parameters.

In general, the sensitivity of any lung cancer detection method that uses 3D imaging of the type used in method 300 depends on the number of BECs that are 3D imaged. The number of BECs 3D imaged from a patient sample may be determined from the total number of enumerated BECs and may be set at a threshold value so that a pre-selected assay accuracy, such as a pre-selected assay sensitivity is statistically likely to have been attained. Method 300 may continue to analyze cells 10 until reaching a pre-selected threshold value that reflects the total number of enumerated BECs and may be at least 250, at least 400, at least 500 at least 600, at least 700, at least 800, at least 900, at least 1000, at least 1100, at least 1200, at least 1300, at least 1400, at least 1500, at least 2000, at least 2500, or in a range of 250 to 2500, 250 to 2000, 400 to 1900, 600 to 1800, 800 to 1700, 1000 to 1600, 1200 to 1600, or 1300 to 1500.

Method 300 may reach a pre-selected sensitivity more quickly than an analogous method that does not use an abnormal cell 2D classifier and a BEC 2D classifier and, instead, generates a 3D image of every cell or putative cell identified because time is not spent capturing 3D images of cells that are not likely to be indicative of lung cancer.

The assay abnormal cell sensitivity is the percent of cells that are or would be identified as abnormal using known identification methods that are identified as abnormal by the AI-based cell classification method 300. The assay abnormal cell sensitivity may be approximated by multiplying the 2D abnormal cell sensitivity by the 3D abnormal cell sensitivity. The assay abnormal cell specificity is the percent of cells that are or would be identified as normal using known identification methods that are identified as normal by the AI-based cell classification method 300. The assay abnormal cell sensitivity may be approximated by multiplying the 2D abnormal cell specificity by the 3D abnormal cell specificity.

Meyer, M. G., et al. (2015), The CELL-CT® 3-dimensional cell imaging technology platform enables the detection of lung cancer using the noninvasive LuCED sputum test. *Cancer Cytopathology*, 123: 512-523 (doi.org/10.1002/cncy.21576); Wilbur, D. C., et al. (2015), Automated 3-dimensional morphologic analysis of sputum specimens for lung cancer detection: Performance characteristics support use in lung cancer screening. Cancer Cytopathology, 123: 548-556 (doi.org/10.1002/cncy.21565); U.S. Pat. Nos. 6,519,355, 6,522,775, 6,591,003, 6,636,623, 6,697,508, 7,197,355, 7,494,809, 7,569,789, 7,738,945, 7,811,825, 7,835,561, 7,867,778, 7,787,112, 7,907,765, 7,933,010, 8,090,183, 8,155,420, 8,947,510, 9,594,072, U.S. Ser. No. 10/753,857, U.S. Ser. No. 11/069,054, and US20200018704, are each incorporated by reference herein in its entirety and specifically as it relates to the components, basic operation, including potential cell staining and enrichment, image formation, including formation of pseudo-projection images, and 3D classifiers of optical tomography systems and lung cancer detection methods and systems described herein.

Training Methods

The present disclosure further includes a method 500 as set forth in the flow chart of FIG. 5, for training 2D cell classifiers which may be used in method 200, method 300, or method 310. 2D classifier training is governed by a binary ground truth; for the abnormal cell 2D classifier, the cell either has abnormal features or does not have abnormal features, while for the BEC 2D classifier, the cell either has BEC-like features or does not have BEC-like features.

Elements of the optical tomography system 100 are referenced in this description of the training method 500 as examples. Similar components of different optical tomography systems may also be used in connection with the training method 500. However, the trained values generated using training method 500, as implemented in the abnormal cell 2D classifier and the BEC 2D classifier, may be most useful when used with the same optical tomography system used in training method 500, or with an optical tomography system with identical or highly analogous components and with performance specifications that are not likely to produce differences in any results that are outside of pre-selected accuracies.

In step 510, an optical tomography system 100 is used, for example, according to steps 400 and 410 of method 310, to generate a set of abnormal cell representative 2D images of a plurality of cells identified as abnormal by a known identification method, such as cytology, a set of BEC representative 2D images of a plurality of cells identified as BECs by a known identification method, and a set of normal/non-BEC representative 2D images of a plurality of lung sample cells that are identified as normal and not BECs by a known identification method. In some embodiments, for training purposes, a cell is identified as abnormal by a known identification method if it is confirmed by a cytopathologist to be in one of the following diagnostic categories: 1) atypia, dysplasia, pre-cancerous cell, malignant cell, or 2) pleomorphic parakeratosis, type II pneumocyte. In some embodiments, for training purposes, a cell is identified as a BEC by a known identification method if it is confirmed by two cytopathologists independently to be a BEC. In some embodiments, a cell is identified as normal if it is randomly acquired from a patient sample and identified as such by a cytopathologist because it does not meet abnormal cell criteria, and a cell is identified as a non-BEC if any cytopathologist identifies the cell as not a BEC.

Cells for training purposes may, in some embodiments, be acquired from the same type of patient sample (e.g., sputum) or prepared in the same manner (e.g., placed in the same optical medium or stained with the same stain) as used in connection with the AI-based cell classification methods and systems that will be operated using the trained values.

Although method 500 illustrates concurrent training of the abnormal cell 2D classifier and the BEC 2D classifier for simplicity, the 2D cell classifiers may be trained separately, optionally using separate training cell sets, as is discussed in the Examples.

In step 520, a processor computes a plurality of cell feature measurements for each of the plurality of cells using the representative 2D image of the cell generated in step 510.

In step 530, the processor performs a regression between the cell feature measurements and the known identifier (i) abnormal, ii) BEC, or iii) normal and non-BEC, or in methods that separately train the 2D cell classifiers iii) normal or non-BEC, whichever is the opposite of the other known identifier used) of the cell to designate an abnormal 2D cell classification score and a BEC 2D cell classification score for each cell.

In step 540, the processor designates a test identifier of i) having abnormal features, ii) having BEC-like features, or iii) not having abnormal or BEC-like features based on the abnormal 2D cell classification score and the BEC 2D classification score for each cell.

In step 550, the respective test identifier is compared to the respective known identifier for each cell to calculate accuracy of both 2D cell classifiers.

In step 560, the accuracy of the 2D cell classifiers may be compared to pre-selected accuracy requirements and, if accuracy requirements are met, designating the 2D cell classifiers as trained, or, if the accuracy requirements are not net, in step 570 adjusting a parameter of the regression for the 2D cell classifier that does not meet accuracy requirements and repeating steps 530 through 560 for at least the adjusted 2D cell classifier.

In some embodiments, the processor adjusts the 2D cell classifier algorithm using Adaptively Boosted Logistic Regression, Random Forest, Decision Trees, or any combination thereof. Adaptively Boosted Logistic Regression uses logistic regression in an iterative loop to improve overall classification merit.

In some embodiments, the pre-selected 2D abnormal cell sensitivity value may be at least 90%, at least 95%, or in a range of 90% to 100%, 90% to 99.9%, 90% to 99%, 90% to 98%. 95% to 100%, 95% to 99.9%, 95% to 99%, or 95% to 98%, or any other 2D abnormal cell sensitivity value recited herein for an abnormal cell 2D classifier.

In some embodiments, the pre-selected 2D abnormal cell specificity value may be at least 65%, at least 70%, at least 75%, or in a range of 65% to 100%, 65% to 99%, 65% to 90%, 65% to 80%, 65% to 75%, 70% to 100%, 70% to 99%, 70% to 90%, 70% to 80%, 70% to 75%, 75% to 100%, 75% to 90%, or 75% to 80%, or any other 2D abnormal cell specificity value recited herein for an abnormal cell 2D classifier.

In some embodiments, the pre-selected 2D BEC sensitivity value may be at least 85%, at least 90%, at least 95%, or in a range of 85% to 100%, 85% to 99.9%, 85% to 99%, 95% to 90%, 90% to 100%, 90% to 99.9%, 90% to 95%, 95% to 100%, 95% to 99.9%, or 95% to 99% or any other 2D BEC sensitivity value recited herein for a BEC 2D classifier.

In some embodiments, the pre-selected 2D BEC specificity value may be at least 60%, at least 65%, at least 70%, or in a range of 60% to 100%, 60% to 99%, 60% to 90%, 60% to 80%, 60% to 75%, 60% to 70%, 60% to 65%, 65% to 100%, 65% to 99%, 65% to 90%, 65% to 80%, 65% to 75%, 65% to 70%, 70% to 100%, 70% to 99%, 70% to 90%, 70% to 80%, or 70% to 75%, or any other 2D BEC specificity value recited herein for a BEC 2D classifier.

Throughout the specification, claims, and drawings, the following terms take the meaning explicitly associated herein, unless the context clearly dictates otherwise. The term "herein" refers to the specification, claims, and drawings associated with the current application. The phrases "in one embodiment," "in another embodiment," "in various embodiments," "in some embodiments," "in other embodiments," and other variations thereof refer to one or more features, structures, functions, limitations, or characteristics of the present disclosure, and are not limited to the same or different embodiments unless the context clearly dictates otherwise.

In the present description, any concentration range, percentage range, ratio range, or integer range is to be understood to include any values or subranges within the recited range unless otherwise indicated. It should also be noted that the term "or" is generally employed in its sense including "or" (i.e., to mean either one, both, or any combination thereof of the alternatives) unless the content dictates otherwise. Also, as used in this specification and the appended claims, the singular forms "a," "an," and "the" include plural referents unless the content dictates otherwise. The terms "include," and "have" and their variants are used synonymously and are to be construed as non-limiting. The term "a combination thereof" as used herein refers to all possible combinations of the listed items preceding the term. For example, "A, B, C, or a combination thereof" is intended to refer to any one of: A, B, C, AB, AC, BC, or ABC. Similarly, the term "combinations thereof" as used herein refers to all possible combinations of the listed items preceding the term. For instance, "A, B, C, and combinations thereof" is intended to refer to all of: A, B, C, AB, AC, BC, and ABC.

EXAMPLES

Example 1

Training of 2D Cell Classifiers

A lung cancer detection method was implemented using a CELL-CT® optical tomography system. The lung cancer detection method was designed to detect lung cancer in a pre-invasive stage, when treatment is easier and more likely to be successful.

The following method was used:

1. Patient sample for testing was fixed, stained and enriched for BECs.
2. Patient sample was then suspended in an oil-based optical medium. The cells in the optical medium were then inserted into a glass micro-capillary tube of approximately 60 μm inner diameter. Pressure was applied to the medium to move the cells into the optical path of a high-magnification microscope in the optical tomography system. (See FIG. 1).
3. Once the cells were in the optical path of the high-magnification microscope, cell search mode was initiated. When in Cell Search mode the CELL-CT® continuously swept its plane of focus, in 1 μm steps, through the lumen of the micro-capillary tube to identify the linear, radial and angular position of cells. Detected dark objects beyond a certain size were identified for potential 3D capture. The 2D image set was filtered to take the central image of a cell. This 2D image was then evaluated using the 2D cell classifiers to determine if the cell had abnormal features or BEC-like features as described below.
4. Each cell was also analyzed in projection image capture mode, during which the tube was rotated so that the optical tomography system generated 500 high-resolution images of the same diagonal cross-section of the capillary tube, taken over 360 degrees of tube rotation. These images were pseudo-projection images, which are simulations of projection images created by integrating the light from the objective lens as the focal plane was swept through the nucleus of any cell contained in the images. The pseudo-projection images thus represented the entire nuclear content in a single image, taken from a single perspective.
5. Pseudo-projection images were processed to correct for residual noise and motion artifact.
6. The corrected pseudo-projection images were processed using filtered back projection to yield a 3D tomographic representation of the cell, also referred to as a 3D image. 3D tomographic representations were created for a substantial number of cells, including multiple cells identified in an optical medium volume within the optical path of the high-magnification microscope before the optical medium is advanced to a different volume by pressure. An example of such a 3D image for both squamous intermediate and dysplastic cells is shown in FIG. 6.
7. The 3D images were evaluated by a cytopathologist to determine if the cell was abnormal, a BEC, or normal, or not a BEC.

An abnormal 2D cell classification score designated the likelihood that the object under investigation had abnormal features. The abnormal 2D cell classification score for a number of cells imaged was used to prepare a composite abnormal 2D cell classification score, which determined whether the patient likely has lung cancer.

The BEC 2D cell classification score designated the likelihood that the object under investigation had BEC-like features. The BEC classification score for a number of cells imaged was used to prepare a composite BEC 2D cell classification score, which helped determine how many BECs had been analyzed.

An abnormal cell 2D classifier and a BEC 2D classifier for use in the lung cancer detection method were trained and tested. Images of cells obtained as described above were
used by cytopathologists employing conventional, known
cell identification methods to designate a known identifier
for each cell also given a test identifier in the training
method.

The abnormal cell 2D classifier development followed a
supervised learning process that was governed by binary
known identifiers (abnormal/normal or having abnormal
features/not having abnormal features). A cell was desig-
nated with the known identifier "abnormal" or "having
abnormal features" if it was confirmed to be in one of the
following diagnostic categories by a cytopathologist:

Atypia, dysplasia, pre-cancerous cell, malignant cell
Pleomorphic parakeratosis, type II pneumocyte.

A cell was designated as not having abnormal features or
"normal," if it was randomly acquired and was designated as
normal by a cytopathologist (due to the absence of the
abnormal criteria identified above).

The BEC 2D classifier development followed a super-
vised learning process that was governed by binary known
identifiers (BEC/non-BEC, or having BEC-like features/not
having BEC-like features). A cell was designated with the
known identifier "BEC" or "having BEC-like features"
when two cytotechnologists independently agreed that it was
a BEC.

A cell categorized as non-BEC by any cytopathologist
was designated with the known identifier "non-BEC" or "not
having BEC-like features."

For training purposes, only the designation "not having
abnormal features" was used with the abnormal cell 2D
classifier and only the designation "not having BEC-like
features" was used with the BEC 2D classifier, however
even during training, a cell may be designated as not having
abnormal features or BEC-like features.

Having abnormal features was designated as 1 for both
the known identifier and the test identifier. Not having
abnormal features was designated as 0 for both the known
identifier and the test identifier. A training set of 16,046 cells
were imaged and provided known identifiers by
cytopathologists and test identifiers by the abnormal cell 2D
classifier. To provide the test identifiers, the cell and nucleus
were segmented from the block of voxels that contained the
cell and features were automatically measured by the optical
tomography system for each cell then used to designate a test
identifier. The test identifier for each cell was then compared
to the known identifier to determine if the test identifier was
correct. This aggregate data set formed the training set to
create the abnormal cell 2D classifier. Adaptively boosted
logistic regression (Ada-boost) was used to refine the abnor-
mal cell 2D classifier. Ada-boost uses logistic regression in
an iterative loop to improve overall classification merit.
Cross-validation was used to limit the complexity of the
model to ensure that it generalized.

The trained abnormal cell 2D classifier was used to
classify cells that were not a part of the training set. Results
showing the known identifier and corresponding test iden-
tifier for the trained abnormal cell 2D classifier are presented
in Table 1 and FIG. 7.

The 2D abnormal cell sensitivity was 95% and the 2D
abnormal cell specificity was 74.7%. Sensitivity was
required to be greater than 90% and specificity was required
to be greater than 65% for the abnormal cell 2D classifier to
be considered trained, so the trained abnormal cell 2D
classifier exceeded pre-selected accuracy values.

TABLE 1

ABNORMAL CELL 2D CLASSIFIER TRAINING SET

|  | Class 0 (Test) | Class 1 (Test) | Total |
|---|---|---|---|
| Class 0 (Known) | 11565 | 3922 | 15487 |
| Class 1 (Known) | 27 | 532 | 559 |
| Total | 11592 | 4454 | 16046 |

FIG. 7 shows the cumulative probability density curve for
the trained abnormal cell 2D classifier using the results of
Table 1. For cells having a known identifier of having
abnormal features, 93.3% (1−0.067) received a correct test
identifier (red line) and were then imaged in 3D. 96.2% of
cells having a known identifier of having BEC-like features
(green line) were then subject to identification by the BEC
2D classifier, and 87.5% of cells having a known identifier
of not having BEC-like features (light blue line) were then
subject to identification by the BEC 2D classifier. Thus,
12.5% of miscellaneous cells (cells not having abnormal or
BEC-like features) were eventually subject to 3D imaging.

Having BEC-like features was designated as 1 for both
the known identifier and the test identifier. Not having
BEC-like features was designated as 0 for both the known
identifier and the test identifier. A training set of 12,572 cells
were imaged and provided known identifiers by
cytopathologists and test identifiers by the BEC 2D classi-
fier. To provide the test identifiers, the cell and nucleus were
segmented from the block of voxels that contained the cell
and features were automatically measured by the optical
tomography system for each cell then used to designate a test
identifier. The test identifier for each cell was then compared
to the known identifier to determine if the test identifier was
correct. This aggregate data set formed the training set to
create the BEC 2D classifier. Adaptively boosted logistic
regression (Ada-boost) was used to refine the abnormal cell
2D classifier. Ada-boost uses logistic regression in an itera-
tive loop to improve overall classification merit. Cross-
validation was used to limit the complexity of the model to
ensure that it generalized.

The trained BEC 2D classifier was used to classify cells
that were not a part of the training set. Results showing the
known identifier and corresponding test identifier for the
trained BEC cell classifier are presented in Table 2 and FIG.
8.

The 2D BEC sensitivity was 88% and the 2D BEC
specificity was 66%. Sensitivity was required to be greater
than 85% and specificity was required to be greater than
60% for the BEC 2D classifier to be considered trained, so
the trained BEC 2D classifier exceeded pre-selected accu-
racy values.

TABLE 2

BEC 2D CLASSIFIER TRAINING SET

|  | Class 0 (Test) | Class 1 (Test) | Total |
|---|---|---|---|
| Class 0 (Known) | 5960 | 3061 | 9021 |
| Class 1 (Known) | 426 | 3125 | 3551 |
| Total | 6386 | 6186 | 12572 |

FIG. 8 shows the cumulative probability density curve for
the trained BEC 2D classifier using the results of Table 2.
For cells having a known identifier of having BEC-like
features, 86.6% (1−0.134) received a correct test identifier (green line) and were then imaged in 3D. For cells having a known identifier of not having BEC-like features, 81% received a correct test identifier (light blue line).

The cumulative results of FIG. 7 and FIG. 8 are as follows:

93.3% of cells having abnormal features (based on the known identifier) were imaged in 3D;

5.8% (1−0.962)+0.866*0.962*100%=89% of cells having BEC-like features (based on the known identifier) were imaged in 3D; and 0.875*0.81*100%=71% of cells not having abnormal features or BEC-like features were imaged only in 2D.

Example 2

Evaluation of 2D Cell Classifiers

The trained 2D cell classifiers were subjected to three independent tests following development to ensure robustness. In each test, the lung cancer detection method was performed using the trained 2D classifiers and a trained 3D classifier, but, as during training in Example 1, was set to acquire 3D images of all objects for which 2D images were obtained so that accuracy could be assessed.

Algorithm Verification Study

The trained 2D cell classifiers were embedded in executable code that also implemented the remainder of the standard lung cancer test and tested using cells from five adenocarcinoma and two squamous carcinoma cell lines. Various measures of accuracy were assessed. The abnormal cell referral rate was 98.7%. The BEC 2D classifier exhibited a BEC 2D sensitivity of 90% and a BEC 2D specificity of 44%.

Pilot Clinical Accuracy Study (CAS)

The Pilot CAS was conducted using a set of specimens that was like the ones used to train the 2D cell classifiers to evaluate the referral rates of the 2D cell classifiers. 34 specimens represented by 267,659 cells were tested. The abnormal cell referral rate was calculated to be 95%. The BEC referral rate was 91%. The abnormal cell referral rate and BEC referral rate demonstrated that training of the 2D algorithms generalized well to a population of cells that were not a part of the training process. Case level accuracy (whether the patient was positive or negative for cells indicative of lung cancer) was not altered by use of 2D cell classifiers and exclusion of some cells from 3D imaging.

CAS-A

A CAS-A study was conducted to further evaluate performance of the 2D cell classifiers. 38 specimens represented by 757,627 cells were tested as in the Pilot CAS. The abnormal cell referral rate was calculated to be 90% by pooling data with that from the Pilot CAS because there were too few abnormal cells in the CAS-A. The BEC referral rate was calculated to be 87%.

The 2D rejection rate was not specified, but it was estimated at 53% during training of the 2D cell classifiers. The measured 2D rejection rate in the CAS-A study was 60%, and the median 2D rejection rate by case was 52%.

Clinical Results Summary

Overall the abnormal cell referral rate and the BEC referral rate met specifications, while the 2D rejection rate was elevated over values measured in training. This demonstrates that training of the 2D cell classifiers generalized well to a population of cells that were not a part of the training process.

Example 3

Test Duration

When a lung cancer detection method according to the present disclosure, using 2D cell classifiers to eliminate some cells from 3D imaging, was conducted and the optical tomography image acquisition portion of the AI-based cell classification method was compared to the optical tomography image acquisition portion of the prior cell classification method in which all cells were 3D imaged, a 52% reduction in cells to 3D image by patient was observed, with a 45% reduction in method duration, while pre-selected accuracies were maintained.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Patent Application Ser. No. 63/394,550, filed Aug. 2, 2022, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An artificial intelligence (AI)-based cell classification method comprising:

a) generating, by an optical tomography system, a representative 2D image of a cell from a patient sample comprising a plurality of cells;

b) evaluating the representative 2D image using an abnormal cell 2D artificial intelligence classifier to determine if the cell has abnormal features;

c) evaluating the representative 2D image using a Bronchial Epithelial Cell (BEC) 2D artificial intelligence classifier to determine if the cell has Bronchial Epithelial Cell (BEC)-like features; and d) generating, by the optical tomography system, a 3D image of the cell if the cell is determined to have abnormal features or to have BEC-like features.

2. The method of claim 1, wherein a 3D image of the cell is not generated if the cell is determined to not have abnormal features and to not have BEC-like features.

3. The method of claim 1, further comprising:

e) repeating a) to d) for a subset of cells within the plurality of cells to generate patient sample data that reflects a total number of enumerated analyzed cells having abnormal features, a total number of enumerated analyzed cells having BEC-like features, or a total number of enumerated analyzed cells.

4. The method of claim 3, further comprising:

f) comparing the total number of enumerated analyzed cells having BEC-like features to a threshold value to determine if the total number of enumerated analyzed cells having BEC-like feature is adequate for an accurate assay because the total number is at or above the threshold value, or if the total number of enumerated analyzed cells having BEC-like features is inadequate for an accurate assay because the total number is below the threshold value.

5. The method of claim 4, further comprising repeating a) to f) until the total number of enumerated analyzed cells having BEC-like features is adequate to detect the presence of cells indicative of lung cancer in the patient sample with a pre-selected accuracy.

6. The method of claim 5, wherein the threshold value is pre-selected by the number of enumerated cells having BEC-like features is statistically likely to detect the presence of cells indicative of lung cancer in the patient sample with the pre-selected accuracy.

7. The method of claim 1, wherein the threshold value is in a range of 250 to 2500 enumerated cells with BEC-like features, 400 to 1900 enumerated cells with BEC-like features, 600 to1800 enumerated cells with BEC-like features, 800 to 1700 enumerated cells with BEC-like features, 1000 to 1600 enumerated cells with BEC-like features, 1200 to 1600 enumerated cells with BEC-like features, or 1300 to 1500 enumerated cells with BEC-like features.

8. The method of claim 1, wherein the threshold value is at least 250 enumerated cells with BEC-like features, at least 400 enumerated cells with BEC-like features, at least 500 enumerated cells with BEC-like features, at least 600 enumerated cells with BEC-like features, at least 700 enumerated cells with BEC-like features, at least 800 enumerated cells with BEC-like features, at least 900 enumerated cells with BEC-like features, at least 1000 enumerated cells with BEC-like features, at least 1100 enumerated cells with BEC-like features, at least 1200 enumerated cells with BEC-like features, at least 1300 enumerated cells with BEC-like features, at least 1400 enumerated cells with BEC-like features, at least 1500 enumerated cells with BEC-like features, at least 2000 enumerated cells with BEC-like features, or at least 2500 enumerated cells with BEC-like features.

9. The method of claim 1, wherein the method has one or more of: a pre-selected 2D abnormal cell sensitivity value of at least 90%, a pre-selected 2D abnormal cell specificity value of at least 65%, a pre-selected 2D BEC sensitivity value of at least 85%, and a pre-selected 2D BEC specificity value of at least 60%.

10. The method of claim 1, wherein the patient sample is obtained from a sputum specimen.

11. The method of claim 1, wherein the patient sample is obtained by isolating and preserving a plurality of cells from the sputum specimen.

12. The method of claim 1, wherein the patient sample comprises abnormal cells, BECs, squamous cells, monocytes, lymphocytes, polymorphonuclear leukocytes, other white blood cells, debris, cell fragments, cell clusters and any combinations thereof.

13. The method of claim 12, wherein abnormal cells are selected from a group consisting of cells exhibiting atypia, dysplastic cells, pre-cancerous cells, pleomorphic parakeratosis, type II pneumocyte abnormal squamous cells, adenocarcinoma cells, bronchioloalveolar carcinoma cells, abnormal neuroendocrine cells, small cell carcinoma cells, non-small cell carcinoma cells, tumor cells, neoplastic cells, bronchioloalveolar carcinoma cells, and any combination thereof.

14. The method of claim 1, further comprising, prior to a), pre-processing the patient sample to stain the plurality of cells with an agent that facilitates generating the representative 2D image, evaluating the representative 2D image using the abnormal cell 2D classifier, or evaluating the representative 2D image using the BEC 2D classifier.

15. The method of claim 1, further comprising, prior to a), enriching the patient sample for BECs or cells likely to be indicative of cancer.

16. The method of claim 1, further comprising, prior to a),
    i) embedding the patient sample in an optical medium and injecting the optical medium with embedded sample into a capillary tube; and
    ii) loading the capillary tube into the optical tomography system so that the capillary tube is between an illumination source and objective lens of the optical tomography system.

17. The method of claim 1, wherein generating, by the optical tomography system, the 2D image of the cell comprises the optical tomography system sweeping a focal plane of the optical tomography system in 1 μm steps across a single cell to generate a single-plane 2D image of the single cell at each step, compiling a set of single-plane 2D images of the single cell, and filtering the set of single-plane 2D images of the single cell to generate the representative 2D image of the cell.

18. The method of claim 17, wherein the representative 2D image of the cell is an image of a central portion of the cell.

19. The method of claim 1, wherein evaluating the representative 2D image using an abnormal cell 2D classifier and evaluating the representative 2D image using a BEC 2D classifier both comprise determining values for a plurality of cell feature measurements.

20. The method of claim 19, wherein the cell feature measurements comprise object shape features, cell-shape features, cytoplasm features, cell nucleoli features, distribution of chromatin, nuclear-size features, nuclear-texture features, other morphometric elements, or any combination thereof.

21. A cell classification system comprising:
    an optical tomography system operable to:
        generate a representative 2D image of a cell from a patient sample; and
        generate a 3D image of the cell if the cell has abnormal features or Bronchial Epithelial Cell (BEC)-like features; and
    a processor operable to:
        compare the representative 2D image of the cell to an abnormal cell 2D artificial intelligence classifier to determine if the cell has abnormal features; and
        compare the representative 2D image of the cell to a Bronchial Epithelial Cell (BEC) 2D artificial intelligence classifier to determine if the cell has BEC-like features.

* * * * *